United States Patent
Oif et al.

(10) Patent No.: US 11,779,777 B1
(45) Date of Patent: Oct. 10, 2023

(54) UV THERAPY PROTOCOL FOR TREATMENT OF NON-DERMATOLOGICAL AUTOIMMUNE CONDITIONS

(71) Applicant: Lumavive LLC, Beachwood, OH (US)

(72) Inventors: Kenneth N. Oif, Beachwood, OH (US); Michael G. Kaufman, Pepper Pike, OH (US)

(73) Assignee: LumaVive LLC, Beachwood, OH (US)

( * ) Notice: Subject to any disclaimer, the term of this patent is extended or adjusted under 35 U.S.C. 154(b) by 0 days.

(21) Appl. No.: 17/903,343

(22) Filed: Sep. 6, 2022

Related U.S. Application Data

(60) Provisional application No. 63/240,384, filed on Sep. 3, 2021, provisional application No. 63/286,665, filed on Dec. 7, 2021.

(51) Int. Cl.
*A61N 5/00* (2006.01)
*A61N 5/06* (2006.01)
*A61K 38/02* (2006.01)

(52) U.S. Cl.
CPC ............ *A61N 5/0613* (2013.01); *A61K 38/02* (2013.01); *A61N 2005/0626* (2013.01); *A61N 2005/0661* (2013.01)

(58) Field of Classification Search
CPC .......... A61N 5/0613; A61N 2005/0626; A61N 2005/0661; A61K 38/02
See application file for complete search history.

(56) References Cited

U.S. PATENT DOCUMENTS

| | | | |
|---|---|---|---|
| 2008/0125834 A1* | 5/2008 | Hendrix | A61N 5/0616 607/88 |
| 2019/0309044 A1* | 10/2019 | Hecht | C07K 16/2866 |
| 2020/0376292 A1* | 12/2020 | Moffat | A61B 5/445 |

OTHER PUBLICATIONS

Altiner, D., Ilknur, T., Fetil, E., Günes, A. and Özkan, S. (2006), Comparison of weekly and daily incremental protocols of narrowband ultraviolet B phototherapy for psoriasis. Journal of the European Academy of Dermatology and Venereology, 20: 1076-1080. (Year: 2006).*

Mohammad et al, The Vitiligo Working Group recommendations for narrowband ultraviolet B light phototherapy treatment of vitiligo, Journal of the American Academy of Dermatology, vol. 76, Issue 5, 2017, pp. 879-888, ISSN 0190-9622 (Year: 2017).*

* cited by examiner

*Primary Examiner* — Lynsey C Eiseman
*Assistant Examiner* — Ranjani Mari Sundaresan
(74) *Attorney, Agent, or Firm* — Frost Brown Todd LLP

(57) ABSTRACT

Methods for a generally safe and effective therapy to lower excessive and chronic inflammation via the promotion of the body's powerful anti-inflammatory Interleukin-10 cytokine and re-activation of dormant T regulatory cells are provided. The methods balance the safety and efficacy of both Interleukin-10 (IL-10) and Treg optimization with excessive risk of UV overexposure to treat and improve several chronic autoimmune inflammatory conditions.

30 Claims, 5 Drawing Sheets

UV THERAPY PROTOCOL FOR TREATMENT OF NON-DERMATOLOGICAL AUTOIMMUNE CONDITIONS

CROSS-REFERENCE TO RELATED APPLICATIONS

This application claims the benefit of U.S. Application No. 63/240,384, entitled UV THERAPY PROTOCOL FOR TREATMENT OF CHRONIC AUTOIMMUNE CONDITIONS, filed on Sep. 3, 2021 and U.S. Application No. 63/286,665, entitled UV THERAPY PROTOCOL FOR TREATMENT OF RHEUMATOID ARTHRITIS, filed on Dec. 7, 2021, the disclosures of which are both incorporated herein by reference in their entirety.

TECHNICAL FIELD

The systems, methods, and devices provided below generally relate to treating various autoimmune conditions using UV therapy, including non-dermatological autoimmune conditions.

BACKGROUND

Inflammation in the human body is often described as a response to infection or injury. However, the normally protective role of inflammation becomes detrimental when the response becomes excessive in magnitude or duration. While excessive inflammation can clearly be pathogenic, the near-universal association of inflammation often contributes to disease exacerbation. Many experts believe inflammation can be best measured through body's current levels of Interleukin 17 (IL-17).

The IL-17 cytokine family is a part of the adaptive and innate immunity that has significant impact on human immune response to infectious pathogens and is involved in the pathogenesis of inflammatory autoimmune diseases like psoriasis, atherosclerosis, asthma, atopic dermatitis, irritable bowel, rheumatoid arthritis, multiple sclerosis, and others. The biological activities of IL-17 are often the result of synergistic or cooperative effects of IL-17 and other inflammatory cytokines. For example, psoriasis—a chronic, debilitating skin disease affecting millions of Americans—is considered one of the most prevalent immune-mediated inflammatory diseases. Infiltrating immune cells have very important roles in disease pathogenesis. Dendritic and inflammatory T cells are significantly increased in lesional skin. Psoriatic lesions show increased frequencies of IFN-g and IL-17 producing T cells.

Rheumatoid arthritis (RA) is defined as chronic inflammation of synovial fluids of the joints. Key characteristics of RA include inflamed arthritic joints leading to joint and cartilage progressive destruction via the infiltration of CD4+ T cells. Autoantibody-producing plasma cells contribute to increases in the numbers of innate immune cells in dendritic cells, granulocytes, macrophages, and ectopic germinal centers (GC) in joints. High levels of IL-17 in RA patients promote both inflammation and bone degradation. Th17 cells induce the production of pro-inflammatory cytokines such as Tumor necrosis factor alpha (TNF-α), Interleukin 1 beta (IL-1β), and Interleukin 6 (IL-6) from cartilage, synoviocytes, macrophages and bone cells. IL-17 also stimulates the expression of multiple chemokines, such as IL-8/CXCL8, CXCL2, CCL20, CCL2 and CCL7. These chemokines recruit neutrophils, macrophages and lymphocytes to the synovium, thereby enhancing inflammation with more severe joint damage.

Multiple sclerosis (MS) is a chronic inflammatory disease of the central nervous system (CNS) that is characterized by damage to myelinated axons in the CNS, leading to the loss of myelin sheath. Inflammatory processes that cause myelin damage leading to the destruction of oligodendrocytes and axons, with subsequent axonal loss, and transient or permanent loss of neurologic functions, resulting in various types of disabilities of different severity. Th17 cells are considered to be one of the key effectors of MS. Increased expression of IL-17- and Th17-associated transcripts (IL-6, IL-17a) has been demonstrated in MS plaques collected at autopsy.

Regulatory T cells (Tregs) act as the nucleus in enforcing immune tolerance. They are mobilized as essential controller of varieties of immune responses—including allergy, autoimmunity, inflammation, and tumor immunity. Regulatory T cells are usually recognized as a specialized subset of CD4+ T cells functioning in establishment and maintenance of immune tolerance. Three main types of CD4+ regulatory cells include: TGF-β-producing CD4+Th3 cells; IL-10 producing Tr1 (type 1 regulatory T) cells; and CD4+CD25+ Foxp3+ T cells. Among these regulatory cells, CD4+CD25+ Foxp3 regulatory T cells are the most physiologically relevant due to their broad and indispensable roles. Loss of "Foxp3" expression over time impairs the suppressive activity of Tregs. Tregs are capable of suppressing not only conventional T cells, but also B cells, NK cells, dendritic cells, and macrophages via humoral and cell-cell contact mechanisms, critical for human homeostasis.

Interleukin-10 (IL-10) is arguably the most potent anti-inflammatory cytokine in the body. It is a pleotropic cytokine as it regulates the expression of multiple inflammatory mediators elicited from a variety of cell types. It is produced by almost all the innate and adaptive immune cells. These cells also serve as its targets, indicating that IL-10 secretion and action is highly regulated and perhaps compartmentalized. IL-10 has immune response down-regulatory properties, which include suppression of the synthesis of pro-inflammatory cytokines such as interferon, IL-17 and of major histocompatibility complex (MEW) class II expression on monocytes. Given the powerful anti-inflammatory properties of IL-10 and the consequence of impaired IL-10 function in the development a number of experimental disease models, including chronic inflammatory bowel disease, rheumatoid arthritis, psoriasis, systemic lupus erythematosus, multiple sclerosis, transplant rejection, cancer, as well as various infectious diseases, there have been efforts to ascertain the therapeutic potential of recombinant IL-10 against these diseases. However, the effective therapeutic potential of IL-10 is limited due to its very short biological half-life, which necessitates frequent administrations in biomedical applications.

Various efforts directed at systemic administration of IL-10 to modulate autoimmune diseases have produced conflicting and largely inconsequential effects. Many attempts at a solution, whether pharmacological or device-based, have fallen short either from low efficacy or high risk to the patient. A generally safe and effective therapy to lower excessive and chronic inflammation via the promotion of the body's powerful anti-inflammatory Interleukin-10 cytokine and re-activation of dormant T regulatory cells is needed.

There are other pathways of several autoimmune diseases that have been recently targeted by pharmacological agents. One pathway is via sphingosine-1-phosphate (S1P), a highly lipid-chemoattractant which has been shown to affect T cell recirculation in the lymph node. S1l3 binds to the receptors S1P1-5, altering lymphocyte circulation, decreasing peripheral naive and central memory T cell numbers, and increasing immune cells dwell time within the lymph nodes. Fingolimod (FTY720), is one example of a biological medication which works primarily by activation of the sphingosine kinase 1 (SphK1) pathway and production of S1P.

Similarly, sustained UVB exposure of the skin can induce immunomodulatory lipids, systemically alter T cell recirculation and trap memory T cells in the skin-draining lymph nodes. Lymphocytes express low amounts of S1P2-5 but high levels of S1P1, which are required for their egress from lymphoid tissues into the blood. Interference with normal S1P-mediated circulation of lymphocytes can have a significant positive effect on immune response. However, an ongoing therapy to target the S1P pathway can only be effectively utilized if it is able to be delivered in a sustained and safe way for what are generally long-term chronic condition, necessitating new UVB protocols.

BRIEF DESCRIPTION OF THE DRAWINGS

The present disclosure will be more readily understood from a detailed description of some example embodiments taken in conjunction with the following figures.

DETAILED DESCRIPTION

Figure 1:
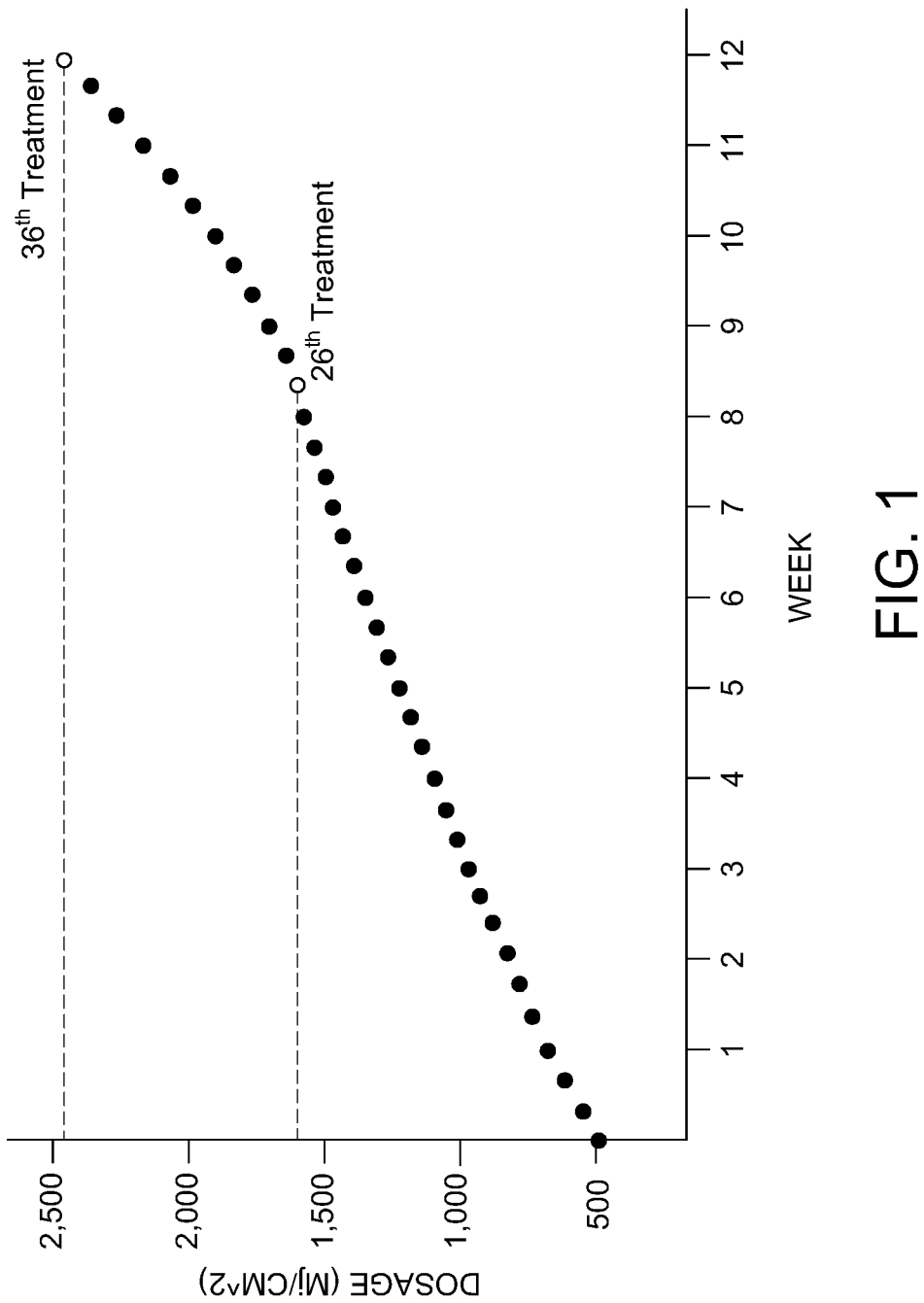
FIG. 1 schematically illustrates a standard course of phototherapy.

Various non-limiting embodiments of the present disclosure will now be described to provide an overall understanding of the principles of the structure, function, and use of the systems, methods, and compositions as disclosed herein. One or more examples of these non-limiting embodiments are illustrated in the accompanying drawings. Those of ordinary skill in the art will understand that systems, methods, and compositions specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

The examples discussed herein are examples only and are provided to assist in the explanation of the systems, methods, and devices described herein. None of the features or components shown in the drawings or discussed below should be taken as mandatory for any specific implementation of any of these systems, methods, and compositions unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Example embodiments described herein can provide phototherapy protocols specifically designed to be a long-term/lifelong solution for maximizing IL-10, T regulatory Cells (Tregs), and other anti-inflammatory molecules. Such phototherapy protocols can seek to safely treat and improve several non-dermatological chronic auto-immune inflammatory disease conditions without incurring unreasonable risk of UV overexposure. Non-limiting example conditions that may be treated in accordance with the present disclosure include, without limitation, atherosclerosis, asthma, irritable bowel or inflammatory bowel disease, ulcerative colitis, Crohn's disease, diabetes type 1, rheumatoid arthritis, vasculitis, multiple sclerosis, and neuropathic pain. Example embodiments of the protocols described herein employ ultraviolet (UV) phototherapy. UV light can improves skin conditions that are caused by an overreaction of the immune system. Skin conditions that are treated with phototherapy include psoriasis (a skin disorder that causes red, scaly patches on the skin), eczema (an itchy, red skin condition, or dermatitis due to allergies), and vitiligo (a skin disorder where normal skin pigment is lost due to destruction of pigment-producing cells by the immune system). In accordance with some embodiments, the condition to be treated is non-dermatological. For example, non-dermatological conditions may cause a deficiency of IL-10 or IL-10 receptor α or β chains, which leads to exacerbation of auto-immune conditions may include, without limitation, atherosclerosis, asthma, irritable bowel or inflammatory bowel disease, ulcerative colitis, Crohn's disease, diabetes type 1, rheumatoid arthritis, multiple sclerosis, and Parkinson's.

UV phototherapy is divided into two modalities based on different wavelengths of light: UVA (320 to 400 nm) and UVB (280 to 320 nm). UVB light has been shown to penetrate less deeply into the lower levels of the skin (i.e., dermis) and cause less long-term damage to the skin. The use of UVB energy induces immunosuppression, both locally through depletion of Langerhans cells, and systemically involving soluble mediators like TNF-α. UVB phototherapy's mechanism of action is a result of direct change of molecular structure in DNA due to photon absorption, which inhibits the DNA transcription machinery and causes cell cycle arrest in human fibroblasts and epidermal cells.

The immunosuppressive effects of the UV light in the skin depend on many different variables, such as the specific wavelength, the radiation intensity, the treatment dose, the number of treatment sessions, and the optics of the human skin. Delayed effects of UV radiation include the inhibition of both the adaptive and innate immune cells that results in immunosuppression. UV light switches off the activity of neutrophils and inhibits the NK cell function, leading to cell apoptosis. These cellular effects are accompanied by altering cytokines leading to the suppression of inflammatory cytokines IL-2, IL-8, IL-9, IL-17, IL-22 and IL-23, TNF-a and IFN-g, and induction of the critically important immunosuppressive cytokine IL-10. UV exposure, keratinocytes, melanocytes, and immune cells that reside in the skin, increase the release of cytokines, such as: TNF-α, IL-6, and IL-10; chemokines such as CCL27 and IL-8; and metabolic products, such as vitamin D, that are involved in the onset of local and systemic effects of UV in complex regulatory loops. Langerhans cells (LC) and other dendritic cells as well as Tregs migrate in and out of the skin and to skin-draining-lymph nodes, thereby coordinating a series of crucial events for the establishment of an immunosuppressive microenvironment.

Example embodiments in accordance with the present disclosure utilize the UVB spectrum of ultraviolet light, which is greater than 280 nm and less than 320 nm, and is not associated with the development of melanoma, the most dangerous form of skin cancer. Efficient repair of DNA damage before replication is a requisite to prevent carcinogenesis to occur. Example embodiments described herein can also address concerns over the risks of significant patient erythema due to the need for increasingly UV exposure levels due to photoadaptation which can lead to very high exposures, while still effectively lowering pro-inflammatory cytokines and promoting anti-inflammatory cytokines.

Human skin possesses several protective mechanisms induced by UV radiation to cope with its adverse effects and to increase the protection against further damage. This process is called photoadaptation and results in a reduction in the severity of the response to exposure to UV radiation, e.g., erythema and DNA damage, usually after a number of repeated exposures. At significant levels of exposure, UVB creates DNA damage (commonly known as sunburn), cyclobutane pyrimidine dimers (CPD), and 6-4 photoproducts. Fortunately, the body's keratinocytes contain DNA repair mechanisms (e.g., nucleotide excision repair (NER)) and anti-oxidant systems to neutralize oxidative stress. NER is responsible for the endogenous protective response to direct DNA photodamage, whereby many cells survive a moderate UVB dose through growth arrest and DNA repair. This protective response not only removes the damage, but also increases the resilience of keratinocytes against a second UVB dose, leading to increased survival of cells that retain their capacity to repair. This protective response is only achieved when the interval between subsequent UVB insults allows sufficient time for the p53 protective program to be induced. When damage is beyond repair, cells go into apoptosis to prevent survival and replication of cells with damaged DNA, which jeopardizes the genomic integrity of the cell. p53 can also exert control over apoptosis by upregulating several apoptosis-related genes including the important IL-10.

An aspect of the present disclosure involves balancing increasing anti-inflammatory cytokines with minimizing the risk of overexposure. Key inflammatory-reducing cytokines are transient. IL-10, as one of the most important cytokines for controlling inflammatory conditions, rises significantly upon DNA damage as a result of UVB phototherapy and is "dose-dependent." After DNA damage, IL-10 has been shown to peak between 16 and 24 hours and return baseline at 24 hours. IL-2 and IL-4 will peak (typically triple) at 32 to 36 hours returning to baseline at 48 hours. IL-4's area under the receiver operating characteristic curve (AUC) is about 5×, and the AUC for IL-6 is 7×base levels.

Studies have shown that, like in most inflammatory conditions, IL-17 in blood serum is significantly elevated compared to healthy controls in severe psoriasis. Studies have also shown IL-10 serum levels after treatment to be higher than those before treatment and that that IL-17 levels decrease after UVB exposure. The release of cytokines and prostanoids is believed to be synchronized and that a slow TH1-to-TH2 shift can occur up to 40 hours after UVB irradiation. To increase IL-10 and improve the activation or function of Tregs while lowering critical inflammatory cytokines like IL-17, the body needs to be continually "challenged," which includes receiving higher doses of UVB energy, until key cytokines return the immune system to homeostasis. An optimal phototherapy protocol should seek to balance maximal efficacy, lowest cumulative dosing, while minimizing the number of treatment sessions to minimize both the number of side effects and cumulative UV energy received.

Standard treatment protocol guidelines from both the United States (American Academy of Dermatology) and Europe are designed for dermatological use and determine a patient's starting treatment energy amount by determining the individual's minimal erythema dose (MED) The MED is defined by how much UV energy it takes for the individual to receive a slightly perceptible "pinkening" of the skin in a small defined test area. The initial treatment "dose" is then be calculated as a percentage of this value (e.g., 70%) while subsequent treatments would be increase by a fixed or percentage (e.g., 40%, 20%, or 10%) amount, until a "maximum dose" is achieved for the current treatment (e.g., 3000 mJ). Current generally-accepted protocols start treatments levels at 50% of MED in Europe or 70% MED in the U.S. while increasing the dosing by fixed percentages, typically continuing until 12 weeks of treatment or until improvements have plateaued, and then suspended. This approach often results in too low of UV dosing and relatively ineffective initial treatment sessions, followed later by too high of dosing in later stages treatments and all-too-often interim overexposure leading to reddening erythema and possible long-term damage. In most conventional protocols, once a patient's lesions have improved, treatments are generally suspended until relapse occurs (often 3 to 6 months). In the current "typical" yearly narrow-band (NB) UVB treatment cycle for moderate to severe psoriasis patients, physicians utilize two courses of treatment, each lasting 12 weeks followed by a pause of 6 months until the psoriasis returns, followed by 12 additional weeks of phototherapy.

The standard protocols often results in very high dosages and risk of serious erythema after only 12 weeks of treatment. While offering likely efficacy for dermatological use, these treatments represent very high amounts of cumulative UV radiation energy as well as the potential for significant treatment erythema (burning) in the event that external factors have not been taken into account for adjusting down the treatment dose. For example, a current standard course of phototherapy generally involves 36 treatment completed over 12 weeks, as schematically illustrated in FIG. 1. Based on the 2019 Joint AAD-NPF Guidelines, a "skin-type III" patient would start at 500 mJ/cm². Based on these protocols, when a patient reaches their 26th treatment (typically seen in week 9 of treatment), they would receive in excess of 1,500 mJ/cm², which would proportionately be increased to an extremely high 2,450 mJ dose at treatment 36. Accordingly, the patient will receive an additional 23,700 mJ over the final 12 treatments of the traditional 36 treatment regimen.

Figure 2:
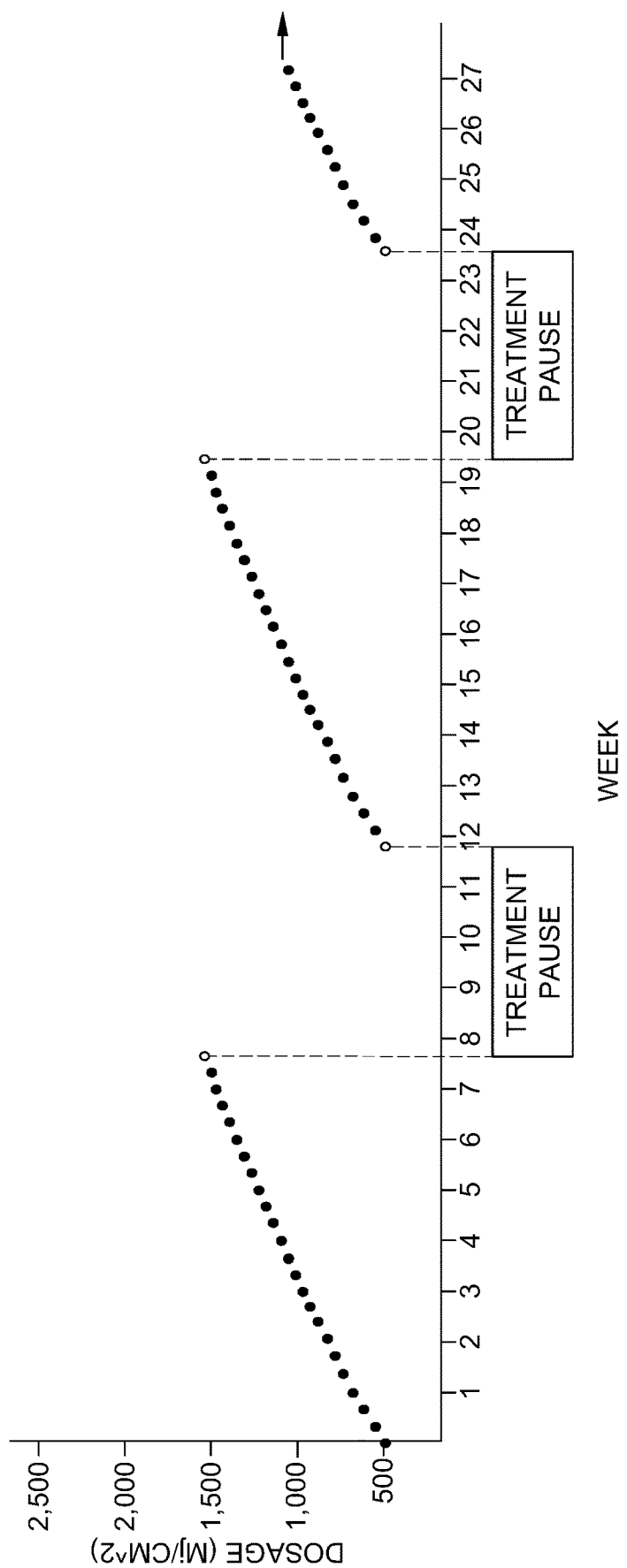
FIG. 2 schematically illustrates an example pause and reset phototherapy protocol in accordance with one non-limiting embodiment.

In some embodiments in accordance with the present disclosure, a "pause and reset" technique can be utilized. For example, rather than continuing with treatments 25 through 36 (i.e., a third month) of phototherapy treatments, a protocol can utilizes a series of pause and reset techniques after 8 weeks of treatment (approx. 24 treatments) by suspending treatment for a fixed time period with the patient returning to their initial treatment dose, which corresponds to their first treatment dose of the regimen. A non-limiting example of a pause and reset protocol is schematically illustrated by FIG. 2, with each set of phototherapy treatments having the same first initial dosage level. In some embodiments, the fixed time period for suspending treatment is 30 days, shown as a treatment pause in FIG. 2, although this disclosure is not so limited. In some examples, the fixed period for suspending treatment can less than 30 days. For example in other embodiments, the fixed period for suspending treatment can between 2 weeks and 3 weeks. In other examples, the fixed period for suspending treatment can be greater than 30 days.

Figure 3:
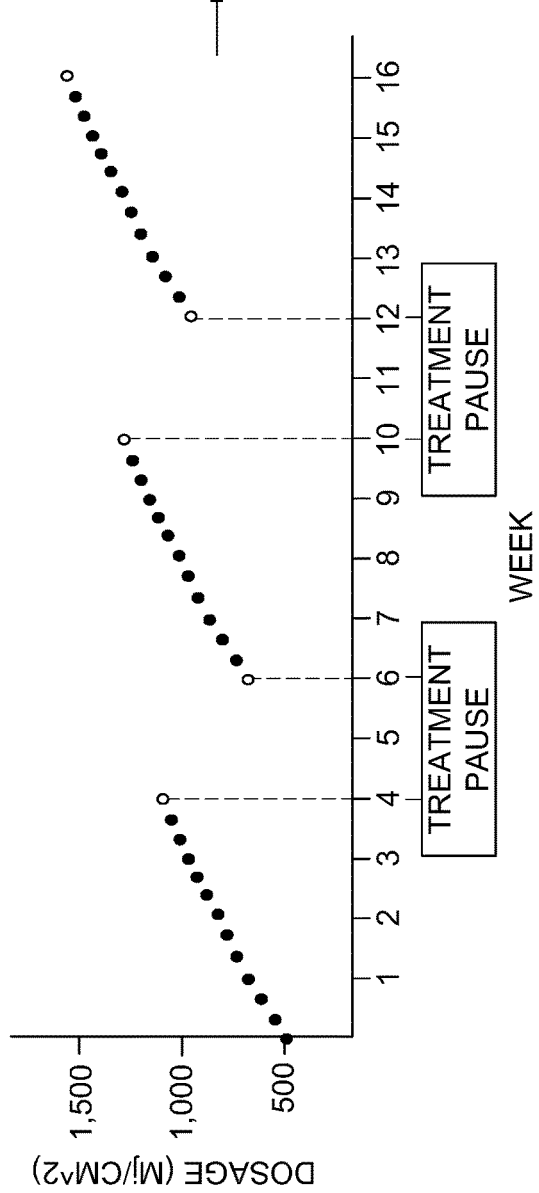
FIG. 3 schematically illustrates another example pause and reset phototherapy protocol in accordance with one non-limiting embodiment.
Figure 4:
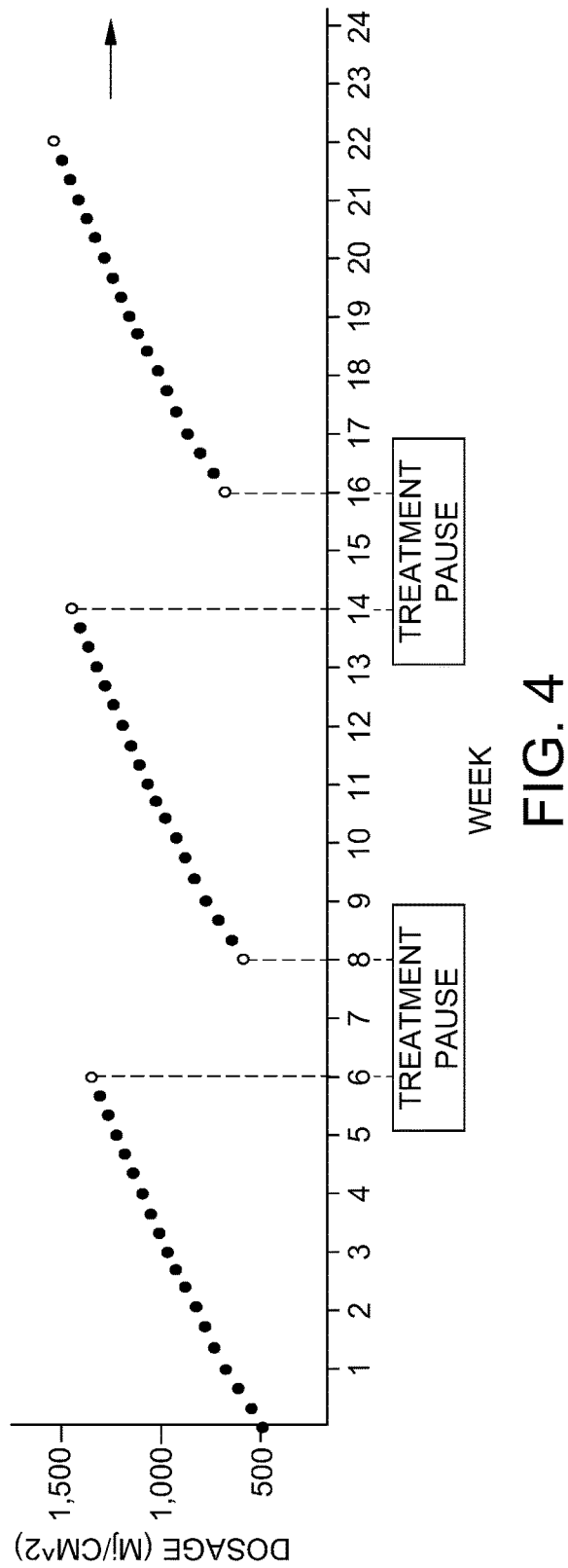
FIG. 4 schematically illustrates yet another example pause and reset phototherapy protocol in accordance with one non-limiting embodiment.
Figure 5:
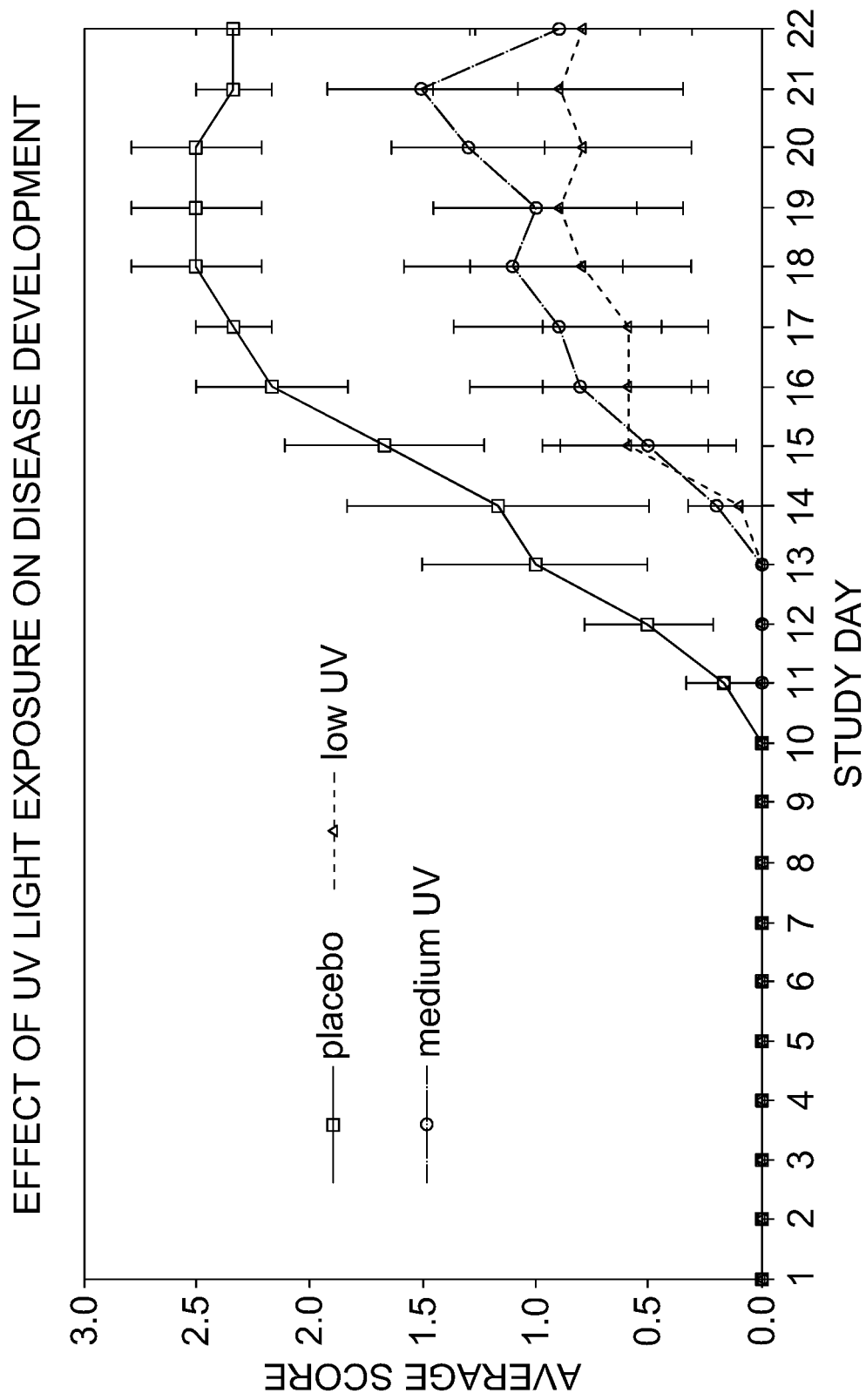
FIG. 5 is chart showing the effect of UV light exposure on disease development in a murine study.
Figure 6:
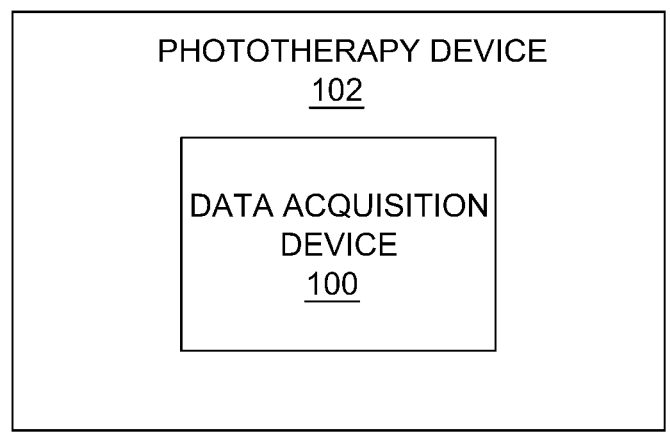
FIG. 6 is a schematic representation of a phototherapy device in accordance with an embodiment.

In another example embodiment, a protocol utilizing a "pause and reset" technique can include the completion of treatments for 28 days, and the suspended of treatment for a period of time, such as 14 days, with the treatment's UV dosing being reduced by 50% (or other suitable amount of dosage reduction) upon commencement on day 42. An example of this pause and reset technique is schematically illustrated in FIG. 3, with each set of phototherapy treatments having an initial dosage level and a final dosage level. As shown, the initial dosage level of a set of phototherapy treatments can be set to 50% of the final dosage level of the preceding set of phototherapy treatments. However, while FIG. 3 depicts a 2:1 ratio of treatment days to pause days and a dosage reduction of 50%, this disclosure is not so limited. For example, such ratio may be in a range of 2:1 through 12:1 and a variety of dosage reductions. FIG. 4 for example depicts an example pause and reset protocol with a ratio greater than 2:1 and a dosage reduction greater than 50%. Additionally, in some embodiments, the ratio can very throughout a treatment cycle as well as the dosage reduction percentage. By way of one non limiting example, a first treatment pause may be 3 weeks and the dosage reduction upon resuming treatment is 60% and a subsequent treatment pause may be 4 weeks and the dosage reduction upon resuming treatment is 40%. By way of another non limiting example, a first treatment pause may be 4 weeks and the dosage reduction upon resuming treatment is 40% and a subsequent treatment pause may be 2 weeks and the dosage reduction upon resuming treatment is 20%.

Example advantages of lowering the amount of required energy and repeating the cycle (e.g., every 90 days) can include reducing possible overexposure and significant erythema and associated risks; reducing cumulative UV radiation that the patient must achieve for each treatment grouping; likely the re-initiation and maximization of critical cytokines for controlling MS like IL-10 each period (e.g., 90 days); and keeping treatment times shorter than if continually having to increase the treatment dose to provide an effectual treatment. For example, if a person with skin type III treated themselves for a full year using a protocol according to an embodiment of the present disclosure, the treatment time can be reduced by over 30 minutes for each session, which would otherwise be a highly risky and potentially dangerous amount of UVB energy.

Chronic conditions, such as psoriasis, atopic dermatitis, multiple sclerosis, vitiligo and others, are often life-long conditions. Conventional UV phototherapy systems were designed to treat dermatological conditions that, while chronic, are episodic in nature. As discussed above, the usage protocols disclosed herein are beneficially useful for the lifelong treatment regimen to care for chronic conditions, whether episodic or not. Accordingly, the "pause and reset" technique in accordance with the present disclosure may be repeated for the duration of treatments, which are generally provided over many years or decades. The anti-inflammatory effects of UVB-NB may benefit patient populations with chronic inflammatory diseases that have a correlation to UV exposure via geographical prevalence, such as diabetes type 1, inflammatory bowel diseases including Crohn's disease and ulcerative colitis, neuropathic pain conditions and vasculitis, which correlate with lower sun exposure and Vitamin D deficiency.

Additional embodiments described herein include using UVB phototherapy treatment in combination with a disease-modifying therapies (DMTs) to speed the efficacy of the DMT alone. For example, multiple sclerosis (MS) is a neurodegenerative disease that currently has more than 10 medications approved by the FDA. However, not all medications will work quickly for all cases of MS. Patients can be on ineffective medications for up to 2 years before monitoring tools can detect disease progression, all the while, irreversible damage to the CNS is happening. Overall, physicians are left with uncertainly in the first few months of a DMT prescription with no response if they should increase the dosage or switch therapies.

Further, patient adherence to a DMT is a critical factor in reducing the amount of damage that MS causes. The primary reasons for poor adherence are negative side effects, financial burden, and administration route that is incompatible with lifestyle (mostly infusions or daily injections). With the delayed onset of effectiveness, low-risk and cheaper drugs are often overlooked. This leaves patients with a high-dose of expensive medication that may work more quickly but leads to greater financial burden or poor adherence due to possible side effects or inability to pay. Significantly lowering overall treatment costs as well as patient out-of-pocket for this disease may improve adherence with this and other DMT medications.

One DMT, glatiramer acetate (GA), has shown to be effective for both clinically isolated syndrome (CIS; precursor to MS) and MS while being one of the safest DMTs available. Studies have shown it to be slow acting during the first six months, which risks additional permanent damage to the patient's myelin sheath caused by the disease until the medication is fully activated. Treatment with GA shows decreases in levels of the proinflammatory Th17 and Th1 cytokines (IL-17, IFN-g, TNF-a, and IL-18) and an increase in the anti-inflammatory/regulatory cytokines (IL-4, TGF, and specifically IL-10) in blood serum but in a delayed fashion at 3 months (a limited 10% increase) and 6 months (55% increase) in clinical responders relative to non-responders. Another DMT, dimethyl fumarate, has been shown to have a delay of action of at least 6 months as seen in the slow increase in anti-inflammatory IL-10 levels as well as slow reduction in pro-inflammatory cytokine IL-18. During these initial 6 months, patients, their families, and physicians are in a "wait and see" pattern, all while potentially irreversible damage is being done to the central nervous system (CNS). Most often, medical insurance providers will not pay for a higher efficacy drug before a lower-efficacy (and cheaper) therapeutic has been demonstrated to be ineffective.

Embodiments described herein, however, may enable faster response to the medication, streamlining the process of finding an effective medication regimen and improving long-term and short-term outcomes. Using UVB phototherapy may shorten the time before the effects of the DMT would otherwise be noticed. In an example embodiment, utilizing a pause and reset UVB phototherapy protocol with a DMT can provide highly significant levels of anti-inflammation cytokines including IL-10 and activated Tregs within 4 weeks of commencing treatment. Example embodiments employ a medical device therapy—UVB phototherapy—in addition to a pharmaceutical treatment. The use of UVB phototherapy in combination with a pharmaceutical DMT may provide synergistic and earlier improvement in inflammatory reduction for diseases like Clinically Isolated Syndrome (CIS; early-stage-MS), IBD, and other chronic autoimmune conditions by increasing levels of key anti-inflammatory cytokines (e.g., IL-10, activated Tregs) and other anti-inflammatory molecules that lower pro-inflammatory cytokines (e.g., IL-17 and IL-18) and other associated pro-inflammatory molecules. In an embodiment, UVB treatments may begin with 3 treatments a week, for example, until the treatments are then paused and reset (e.g., as described above).

In one example embodiment, using UVB phototherapy along with GA may inhibit the progression of MS while significantly reducing treatment cost, which in turn may improve patients' adherence to the treatment regimen. As described herein, UVB-NB phototherapy stimulates critical molecular and anti-inflammatory cellular structures (i.e., cytokines), which are found to be diminished or deficient in CIS patients in a dose-dependent manner. Such a combination therapy can effectively control a patient's MS or CIS to slow disease progression and maintain their independence and quality of life. In some embodiments, the combination therapy can also enable a lower dose of the pharmaceutical treatment (compared to using the pharmaceutical alone), which can reduce side effects and lead to greater adherence. While the embodiments described herein relate to GA as the pharmaceutical treatment used in combination with the UVB phototherapy, the disclosure is not so limited. The pharmaceutical treatment may be, without limitation, any suitable treatment, such as Interferon beta-1a (IFNβ-1a) and interferon beta-1b (IFNβ-1b), dimethyl fumarate, fingolimod, ocrelizumab, GA, other Th1 altering medications, or a combination thereof. The combination therapy can proceed using a pause and reset protocol in accordance with the present disclosure.

Another advantage of combination therapy of UVB and GA is that no lab screening is not necessarily required. DMTs are limited in their dosing and use cases if a patient is immune-challenged or pregnant. The combination therapy can be positioned at current or future potential pregnant patients as information on more than 7,000 pregnancies have been collected over more than 20 years in Teva's Glatiramer Acetate Pharmacovigilance Database. No higher risk for teratogenic effects has been assessed in pregnancies exposed to GA. As MS affect women four time more than men, UVB-NB therapy with GA can provide a safe and efficacious treatment paradigm.

A mouse trial was conducted to determine the effect of UV light exposure on disease development. The trial confirmed that a UV light treatment device can impact mice receiving MOG35-55 for EAE induction and generate an increased level of IL-10 while causing a reduction of IL-17 levels and associated EAE clinical scores of the cohorts. The trial involved treating murine models of MS at an appropriate UV dose and at an appropriate interval of every other day. UV light treatment appeared to delay the onset of signs of EAE by three days. The lower exposure times also appeared to reduce the incidence to 60% (3 out of 5 animals exhibiting any signs of EAE); an improvement over the placebo (100% incidence) or the longer exposure times (80% incidence). The results, shown in FIG. 1, indicated that low or medium UV treatment was effective in slowing the appearance of disease development and reducing the amount of disease development that occurred. Additionally, the inhibition of symptom formation appeared to be dose-dependent.

Additional embodiments described herein include using UVB phototherapy treatment in combination with a medication. Example medications include, without limitation: Botox (onabotulinumtoxin A); DDAVP Nasal Spray (desmopressin); Detrol (tolterodine); Ditropan (oxybutynin), Ditropan XL; Enablex (darifenacin); Flomax (tamsulosin); Prazosin; Myrbetriq (mirabegron); Oxytrol (oxybutynin); Tofranil (imipramine); Vesicare (solifenacin succinate); Bactrim; Septra (sulfamethoxazole); Cipro (ciprofloxacin); Levaquin (levofloxacin); Macrodantim (nitrofurantoin); Hiprex (methenamine); Pyridium (phenazopyridine); Colace (docusate); Dulcolax (bisacodyl); Enemeez (docusate stool softener laxative); Fleet Enema (sodium phosphate); Mineral Oil; Metamucil (*psyllium* hydrophilic musilloid); Phillips Milk of Magnesia (magnesium hydroxide); Sani-Supp suppository (gylcerin); Celexa (citalopram); Cymbalta (duloxetine hydrochloride); Effexor (velafaxine); Paxil (paroxetine); Prozac (fluoxetine); Wellbutrin (bupropion); Zoloft (sertraline); Antivert (meclizine); Nuedexta (dextromethorphan+quinidine); Adderall (dextroamphetamine and amphetamine); Amantadine; Provigil (modafinil); Prozac (fluoxetine); Ritalin (methylphenidate); Vistaril (hydroxyzine); Cymbalta (duloxetine); Effexor (venlafaxine); Elavil (amitriptyline); Lamictal (lamotrigine); Lyrica (pregabalin); Neurontin (gabapentin); Pamelor; Aventyl (nortriptyline); Tegetrol (carbamazepine); Trileptal (oxcarbazepine); Cialis (tadalafil); Levitra (vardenafil); MUSE (alprostadil); Prostin VR (alprostadil); Stendra (avanafil); Viagra (sildenafil); Baclofen; Botox (onabotulinumtoxin A); Dantrium (dantrolene); Klonopin (clonazepam); Valium (diazepam); Zanaflex (tizanidine); Laniazid—Nydrazid (isoniazid); Klonopin (clonazepam); Ampyra (dalfampridine); and a combination thereof.

Additional embodiments described herein include using UVB phototherapy treatment in combination with a medication to treat rheumatoid arthritis (RA). Example medications include, without limitation: a nonsteroidal anti-inflammatory drug (NSAID), a steroid, a disease modifying antirheumatic drug (DMARD), a biologic agent, or a combination thereof. NSAIDs may be used to relieve pain and reduce inflammation. Example NSAIDs include, without limitation, over-the-counter NSAIDs, such as ibuprofen (e.g., ADVIL, MOTRIN IB, etc.) or naproxen sodium (e.g., ALEVE), prescription strength NSAIDs, or a combination thereof. Corticosteroid medications (e.g., prednisone) may be used to reduce inflammation and pain and slow joint damage. DMARDs may be used to slow the progression of rheumatoid arthritis and save the joints and other tissues from permanent damage. The DMARDs may be a common DMARD, a targeted synthetic DMARD, or a combination thereof. Common DMARDs include, without limitation, methotrexate (e.g., TREXALL, OTREXUP, etc.), leflunomide (ARAVA), hydroxychloroquine (PLAQUENIL), sulfasalazine (AZULFIDINE), or a combination thereof. Targeted synthetic DMARDs include, without limitation, baricitinib (OLUMIANT), tofacitinib (XELJANZ), upadacitinib (RINVOQ), or a combination thereof. Biologic agents, also known as biologic response modifiers, include, without limitation, abatacept (ORENCIA), adalimumab (HUMIRA), anakinra (KINERET), certolizumab (CIMZIA), etanercept (ENBREL), golimumab (SIMPONI), infliximab (REMICADE), rituximab (RITUXAN), sarilumab (KEVZARA), tocilizumab (ACTEMRA), or a combination thereof.

In some embodiments, the medical device therapy may be configured as an at-home treatment. Phototherapy used to treat episodic skin conditions is traditionally performed in a medical setting, which is expensive and not practical for chronic and long-term use that would be required for MS. Phototherapy available in the patient's home provides treatment availability for patients who have challenges with travel for therapy due to disabilities, for example.

In some embodiments, a data acquisition system is used to collect phototherapy usage data. The data acquisition system 100 may be incorporated in a multi-dimensional full body phototherapy unit 102, as shown in FIG. 2. In some embodiments, physicians can remotely access the adherence data to maintain open communication with patients and correct inaccurate use of the treatment.

YKL-40, also known as CH13L1 (chitinase-3-like protein 1), or human cartilage glycoprotein is a member of the mammalian chitinase-like protein family. YKL-40 is produced by macrophages, neutrophils and cancer cells and regulates vascular endothelial growth factor (VEGF). YKL-40 has been associated with inflammation disorders, including arteriosclerosis and general endothelial dysfunction and may be a useful biomarker for determining levels of the inflammation from the various diseases being treated. In accordance with the present disclosure, a treatment protocol for a patient can be based on patient-specific YKL-40 levels. Such YKL-40 levels can be measured, for example, via serum, plasma, sputum or other biological measurements. Such measurement can be used to determine levels of systemic inflammation and the need to adjust the protocol's pause/interval period. In accordance with another embodiment, a ratio or other mathematical comparison of patient-specific YKL-40 levels in conjunction with IL-17 levels can be used to adjust the treatment pause/interval period. Such adjustment can include, for example, lengthening or shortening how long the treatment is suspended. Additionally or alternatively, such adjustment can include adjusting the amount of the UV dosing reduction upon commencement of treatment after being suspended. An additional embodiment may be to use a ratio or otherwise mathematical comparison of patient-specific YKL-40 levels in conjunction with an alternative anti-inflammatory molecule level to adjust the treatment pause/interval period.

As used herein, "treat", "treating" and/or "treatment" refers to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to the particular uses contemplated. The scope is, of course, not limited to the examples set forth herein, but can be employed in any number of applications and equivalent devices by those of ordinary skill in the art. Rather, it is hereby intended that the scope of the invention is to be defined by the claims appended hereto.

What is claimed is:

1. A method of treating a non-dermatological autoimmune condition in a subject with a pause and reset phototherapy protocol, comprising:

administering ultraviolet B (UVB) therapy for a first set of phototherapy treatments having escalating dosage levels over time, the first set of phototherapy treatments having a first initial dosage level, wherein the first set of phototherapy treatments are defined by a pause and reset phototherapy protocol;

pausing treatment for a pause period, wherein the pause period has a length of time that is based on the pause and reset phototherapy protocol, and wherein the length of time is at least about two weeks; and administering UVB therapy for a second set of phototherapy treatments having escalating dosage levels over time, the second set of phototherapy treatments having a second initial dosage level, wherein the second initial dosage level is substantially same as the first initial dosage level, wherein the second set of phototherapy treatments are defined by a pause and reset phototherapy protocol.

2. The method of claim 1, wherein the first set of phototherapy treatments are delivered over a first period of time, wherein the first period of time is defined by the pause and reset phototherapy protocol, and wherein the length of time of the pause period is less than the first period of time.

3. The method of claim 2, wherein the second set of phototherapy treatments are delivered over a second period of time and wherein the first period of time is substantially the same as the second period of time.

4. The method of claim 3, wherein the first set of phototherapy treatments and the second set of phototherapy treatments each comprise less than 30 phototherapy treatments.

5. The method of claim 3, wherein the first set of phototherapy treatments and the second set of phototherapy treatments each comprise 24 phototherapy treatments.

6. The method of claim 2, wherein the first period of time has a ratio to the first pause period in the range of 2:1 to 12:1.

7. The method of claim 6, wherein the length of time of the pause period is based on measured YKL-40 levels of the subject.

8. The method of claim 1, wherein the length of time of the pause period less than about four weeks.

9. The method of claim 1, further comprising:
subsequent to administering UVB therapy for the second set of phototherapy treatments, pausing treatment for a second pause period, wherein the second pause period has a length of time that is based on the pause and reset phototherapy protocol; and
administering UVB therapy for a third set of phototherapy treatments having escalating dosage levels over time, the third set of phototherapy treatments having a third initial dosage level, wherein the third initial dosage level is substantially same as the first initial dosage level and the second initial dosage level, wherein the third set of phototherapy treatments are defined by a pause and reset phototherapy protocol.

10. The method of claim 9, wherein the pause period is a first pause period, and wherein the second pause period has the same length as the first pause period.

11. The method of claim 9, wherein the pause period is a first pause period, and wherein the second pause period has a different length than the first pause period.

12. The method of claim 1, further comprising:
administering a disease-modifying therapy in conjunction with the administration of the first set of phototherapy treatments and the second set of phototherapy treatments.

13. The method of claim 1, further comprising:
administering glatiramer acetate in conjunction with the administration of the first set of phototherapy treatments and the second set of phototherapy treatments.

14. The method of claim 1, wherein the non-dermatological autoimmune condition is rheumatoid arthritis.

15. The method of claim 1, wherein the length of time of the pause period is based on measured YKL-40 levels of the subject.

16. The method of claim 1, wherein the non-dermatological autoimmune condition is Multiple Sclerosis.

17. The method of claim 16, wherein the length of time of the pause period is based on measured YKL-40 levels of the subject.

18. A method of treating a non-dermatological autoimmune condition in a subject, comprising:
administering ultraviolet B (UVB) therapy for a first set of phototherapy treatments having escalating dosage levels over time, the first set of phototherapy treatments having a first initial dosage level and a first final dosage level; and
in conjunction with the administration of the first set of phototherapy treatments, administering a disease-modifying therapy (DMT) to the subject for treatment of the non-dermatological autoimmune condition.

19. The method of claim 18, wherein the non-dermatological autoimmune condition is rheumatoid arthritis.

20. The method of claim 18, wherein the non-dermatological autoimmune condition is Multiple Sclerosis.

21. The method of claim 18, further comprising:
pausing treatment for a pause period, wherein the pause period has a length of time that is based on the pause and reset phototherapy protocol, and wherein the length of time is at least about two weeks; and
administering UVB therapy for a second set of phototherapy treatments having escalating dosage levels over time, the second set of phototherapy treatments having a second initial dosage level and a second final dosage level, wherein the second initial dosage level is less than the first final dosage level, and wherein the second final dosage level is greater than the first final dosage level; and
in conjunction with the administration of the second set of phototherapy treatments, administering the DMT to the subject for treatment of the autoimmune condition.

22. The method of claim 21, wherein the second initial dosage level is less than 75% of first final dosage level.

23. The method of claim 22, wherein the second initial dosage level is about 50% of first final dosage level.

24. The method of claim 21, wherein the first set of phototherapy treatments are delivered over a first period of time and wherein the length of time of the pause period is less than the first period of time.

25. The method of claim 21, wherein the first period of time has a ratio to the pause period in the range of 2:1 to 12:1.

26. The method of claim 21, further comprising:
subsequent to administering UVB therapy for the second set of phototherapy treatments, pausing treatment for a second pause period;
administering UVB therapy for a third set of phototherapy treatments having escalating dosage levels over time, the third set of phototherapy treatments having a third initial dosage level and a third final dosage level, wherein the third initial dosage level is less than the second final dosage level, and wherein the third final dosage level is greater than the second final dosage level; and
in conjunction with the administration of the third set of phototherapy treatments, administering the DMT to the subject for treatment of the non-dermatological autoimmune condition.

27. A method of treating rheumatoid arthritis in a subject with a pause and reset phototherapy protocol, comprising:
administering a medication to treat rheumatoid arthritis;
administering ultraviolet B (UVB) therapy for a first set of phototherapy treatments having escalating dosage levels over time, the first set of phototherapy treatments having a first initial dosage level, wherein the first set of phototherapy treatments are defined by a pause and reset phototherapy protocol;
pausing treatment for a pause period, wherein the pause period has a length of time that is based on the pause and reset phototherapy protocol, and wherein the length of time is at least about two weeks; and
administering UVB therapy for a second set of phototherapy treatments having escalating dosage levels over time, the second set of phototherapy treatments having a second initial dosage level, wherein the second initial dosage level is substantially same as the first initial dosage level, wherein the second set of phototherapy treatments are defined by a pause and reset phototherapy protocol.

28. The method of claim 27, wherein the medication to treat rheumatoid arthritis comprises any of a nonsteroidal anti-inflammatory drug (NSAID), a steroid, a disease modifying antirheumatic drug (DMARD), and a biologic agent.

29. A method of treating rheumatoid arthritis in a subject with a pause and reset phototherapy protocol, comprising:

administering a medication to treat rheumatoid arthritis;

administering ultraviolet B (UVB) therapy for a first set of phototherapy treatments having escalating dosage levels over time, the first set of phototherapy treatments having a first initial dosage level and a first final dosage level, wherein the first set of phototherapy treatments are defined by a pause and reset phototherapy protocol;

pausing treatment for a pause period, wherein the pause period has a length of time that is based on the pause and reset phototherapy protocol, and wherein the length of time is at least about two weeks; and administering UVB therapy for a second set of phototherapy treatments having escalating dosage levels over time, the second set of phototherapy treatments having a second initial dosage level and a second final dosage level, wherein the second initial dosage level is less than the first final dosage level, and wherein the second final dosage level is greater than the first final dosage level, wherein the second set of phototherapy treatments are defined by a pause and reset phototherapy protocol.

30. The method of claim 29, wherein the medication to treat rheumatoid arthritis comprises any of a nonsteroidal anti-inflammatory drug (NSAID), a steroid, a disease modifying antirheumatic drug (DMARD), and a biologic agent.

* * * * *